US012742736B2

(12) United States Patent
Sano et al.

(10) Patent No.: US 12,742,736 B2
(45) Date of Patent: Sep. 22, 2026

(54) CHROMATOGRAPHIC STRIP SUPPORT TOOL AND METHOD FOR USING SAME

(71) Applicant: KANEKA CORPORATION, Osaka (JP)

(72) Inventors: Sotaro Sano, Hyogo (JP); Shigehiko Miyamoto, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 753 days.

(21) Appl. No.: 18/043,767

(22) PCT Filed: Aug. 11, 2021

(86) PCT No.: PCT/JP2021/029612

§ 371 (c)(1), (2) Date: Mar. 2, 2023

(87) PCT Pub. No.: WO2022/050011

PCT Pub. Date: Mar. 10, 2022

(65) Prior Publication Data

US 2023/0349833 A1 Nov. 2, 2023

(30) Foreign Application Priority Data

Sep. 3, 2020 (JP) ................................ 2020-148340

(51) Int. Cl.
*G01N 21/78* (2006.01)
*B01L 3/00* (2006.01)
(Continued)

(52) U.S. Cl.
CPC ............ *G01N 21/78* (2013.01); *B01L 3/5023* (2013.01); *G01N 33/521* (2013.01);
(Continued)

(58) Field of Classification Search
CPC ................ G01N 21/78; G01N 33/521; G01N 2021/7759; G01N 33/54388;
(Continued)

(56) References Cited

U.S. PATENT DOCUMENTS 6,375,897 B1 4/2002 Bachand
8,470,609 B2 * 6/2013 Chen ............... G01N 33/54388 435/7.1

(Continued)

FOREIGN PATENT DOCUMENTS

CN 205263096 U 5/2016
CN 209590046 U 11/2019

(Continued)

*Primary Examiner* — Samuel P Siefke
(74) *Attorney, Agent, or Firm* — IPUSA, PLLC

(57) ABSTRACT

A chromatographic strip support tool (except one that includes a chromatographic strip) is provided. The chromatographic strip support tool includes a support surface that is continuous and on which the chromatographic strip can be placed, a projected portion formed on the support surface and having a first abutting portion that can abut against an extremity of the chromatographic strip placed on the support surface, the extremity being present at one end side of the chromatographic strip, and a display section formed on the support surface and displaying a detection item corresponding to a predetermined location of the chromatographic strip with the chromatographic strip being placed on the support surface in a manner that the extremity of the chromatographic strip abuts against the first abutting portion.

13 Claims, 16 Drawing Sheets

(51) Int. Cl.
*G01N 33/52* (2006.01)
*G01N 21/77* (2006.01)

(52) U.S. Cl.
CPC . *B01L 2300/021* (2013.01); *B01L 2300/0609* (2013.01); *B01L 2300/069* (2013.01); *B01L 2300/0825* (2013.01); *G01N 2021/7759* (2013.01)

(58) Field of Classification Search
CPC ........... G01N 2021/7796; B01L 3/5023; B01L 2300/021; B01L 2300/0609; B01L 2300/069; B01L 2300/0825; B01L 2300/126
See application file for complete search history.

(56) References Cited

U.S. PATENT DOCUMENTS

| | | | |
|---|---|---|---|
| 2003/0205097 A1 | 11/2003 | Wickstead et al. | |
| 2006/0008847 A1* | 1/2006 | Ramel .............. | G01N 33/54389 435/7.1 |
| 2020/0263164 A1 | 8/2020 | Sano et al. | |

FOREIGN PATENT DOCUMENTS

| | | |
|---|---|---|
| CN | 211318461 U | 8/2020 |
| JP | 2003-532054 | 10/2003 |
| JP | 2005-515431 | 5/2005 |
| JP | 2007-033293 | 2/2007 |
| WO | 2019/093353 | 5/2019 |

* cited by examiner

10 viewing location C

13

11

12a

10

22
21
11
14

10

22
21
11
14

10

13
12a
22
11
14

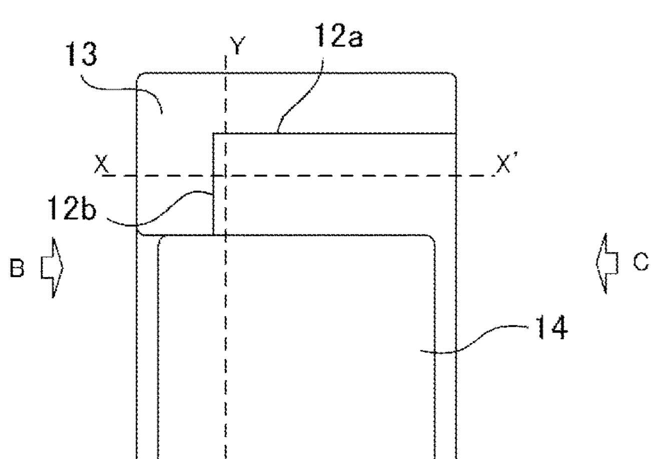
FIG.12
10
13
12b
X
X'
11
FIG.13A
10
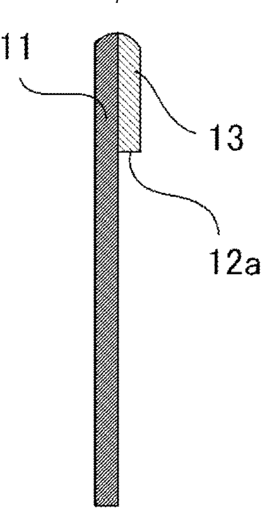
Y'
FIG.13B 10
viewing location A
12b
13

11

18a
18
10
18b
17
16
15
12a
13
11
12b
14

10
13
Y
12a
X
X'
12b
B
C
14
Y'
11
A

10

CHROMATOGRAPHIC STRIP SUPPORT TOOL AND METHOD FOR USING SAME

TECHNICAL FIELD

The present invention relates to a chromatographic strip support tool and a method of using the same.

BACKGROUND ART

Hitherto, for example, immunochromatography and nucleic acid chromatography have been known as the methods for analyzing biological components such as proteins and nucleic acids contained in liquid analytes. Test strips to which the principle of paper chromatography is applied (these test strips may hereinafter be referred to as chromatographic strips) are used in these analyzing methods.

The chromatographic strip includes an analyte supply section to which an analyte is supplied, a membrane section in which the analyte is developed, and an absorption pad section configured to absorb the analyte. After the analyte is supplied to the analyte supply section and developed using a developing solution, a result indicating a successful detection (line coloring) occurs in the membrane section when a predetermined biological component is present. By reading this result, it is possible to detect that the analyte contains the biological component.

To read the line coloring in the membrane section, one may set the chromatographic strip on a determination assisting tool (hereinafter, may be referred to as "chromatographic strip support tool") on which detection items corresponding to the locations of line colorings are written, and visually check the detection item at which a line coloring is seen.

A testing device proposed as a testing device of the existing type using the chromatographic strip includes: for example, a card-shaped support 100 including a printed surface 100*a* displaying detection-related items, an analyte name display field 100*b*, and detection items 100*c*; a test strip 200 secured on the card-shaped support 100 and including a determination region 200*a* corresponding to the membrane section in which a sign indicating a successful detection appears, a liquid absorbing section 200*b* configured to absorb an analyte, and a sample dropping section 200*c*; and a partial cover 300 secured on the card-shaped support 100 with the test strip 200 interposed in between and partially covering the card-shaped support 100 as illustrated in FIG. 20A to FIG. 20C, wherein the partial cover 300 has a dent portion 300*a* in which a dropping hole 300*b* open to the sample dropping section 200*c* of the test strip 200 is formed (for example, see PTL 1).

CITATION LIST

Patent Literature

PTL 1: Japanese Patent Application Laid-Open (JP-A) No. 2007-033293

SUMMARY OF INVENTION

Technical Problem

When a chromatographic strip is set on an existing chromatographic strip support tool, and a detection item at which a result indicating a successful detection (line coloring) is seen is visually checked, there is a problem that the line coloring may be read as something mistaken (detected as something mistaken) due to misplacement of the chromatographic strip.

Moreover, in the existing testing device using the chromatographic strip, the side surface 200*d* of the determination region 200*a* abuts against an opening portion 300*c* of the partial cover 300 as illustrated in FIG. 20D. Therefore, there is a problem that the analyte travels the opening portion 300*c* and smooth development (flow) of the analyte is inhibited.

The present invention aims for solving the various problems in the related art and achieving the object described below. That is, an object of the present invention is to provide a chromatographic strip support tool that minimizes occurrence of mistaken reading (mistaken detection) of a result indicating a successful detection (line coloring) due to misplacement of a chromatographic strip, and does not inhibit smooth development of an analyte, and a method of using the chromatographic strip support tool.

Solution to Problem

Means for solving the above problems are as follows.

<1> A chromatographic strip support tool (except one that includes a chromatographic strip), including:

a support surface that is continuous and on which the chromatographic strip can be placed;

a projected portion formed on the support surface and having a first abutting portion that can abut against an extremity of the chromatographic strip placed on the support surface, the extremity being present at one end side of the chromatographic strip; and a display section formed on the support surface and displaying a detection item corresponding to a predetermined location of the chromatographic strip with the chromatographic strip being placed on the support surface in a manner that the extremity of the chromatographic strip abuts against the first abutting portion.

<2> The chromatographic strip support tool (except one that includes the chromatographic strip) according to <1>, wherein the projected portion has a second abutting portion that can abut against at least a partial portion of a side surface of the chromatographic strip placed on the support surface, the partial portion of the side surface being present at the one end side of the chromatographic strip, the side surface being parallel with a longitudinal direction of the chromatographic strip, and the display section displays the detection item corresponding to the predetermined location of the chromatographic strip with the chromatographic strip being placed on the support surface in a manner that the extremity of the chromatographic strip abuts against the first abutting portion and the side surface of the chromatographic strip abuts against the second abutting portion.

<3> The chromatographic strip support tool (except one that includes the chromatographic strip) according to <2>, wherein when the support surface is seen in a plan view perspective, the first abutting portion and the second abutting portion of the projected portion are at locations at which the first abutting portion and the second abutting portion are orthogonal to each other.

<4> The chromatographic strip support tool (except one that includes the chromatographic strip) according to <3>, wherein when the support surface is seen in the plan view perspective, the first abutting portion and the second abutting portion of the projected portion are at the locations at which the first abutting portion and the second abutting portion are orthogonal to each other and one end of the first abutting portion and one end of the second abutting portion contact each other.

<5> The chromatographic strip support tool (except one that includes the chromatographic strip) according to any one of <2> to <4>, wherein the second abutting portion includes paired portions that can abut against at least partial portions of a pair of side surfaces of the chromatographic strip respectively, the pair of side surfaces being parallel with the longitudinal direction of the chromatographic strip.

<6> The chromatographic strip support tool (except one that includes the chromatographic strip) according to any one of <1> to <5>, wherein the display section displays a plurality of detection items corresponding to a plurality of predetermined locations of the chromatographic strip respectively.

<7> A chromatographic strip support tool (except one that includes a chromatographic strip), including:

a support surface that is continuous and on which the chromatographic strip can be placed; and a foldable portion continuous with the support surface via a folding line, wherein when the foldable portion is folded along the folding line and made to abut against the support surface, the foldable portion becomes fixed in a manner to form a projected portion having a first abutting portion that can abut against an extremity of the chromatographic strip placed on the support surface, the extremity being present at one end side of the chromatographic strip, and the support surface has a display section displaying a detection item corresponding to a predetermined location of the chromatographic strip with the chromatographic strip being placed on the support surface in a manner that the extremity of the chromatographic strip abuts against the first abutting portion.

<8> The chromatographic strip support tool (except one that includes the chromatographic strip) according to any one of <1> to <7>, wherein the projected portion abuts only against an absorption pad section of the chromatographic strip.

<9> A method of using the chromatographic strip support tool according to <1>, the method including:

placing the one end side of the chromatographic strip at the projected portion formed on the support surface of the chromatographic strip support tool in a manner that the extremity of the chromatographic strip at the one end side opposite to a side at which an analyte is supplied and the first abutting portion abut against each other; and in response to a detection at the predetermined location of the chromatographic strip, discerning the detection item of the display section, the detection item being displayed at a location corresponding to the predetermined location at which the detection occurs.

<10> A method of using the chromatographic strip support tool according to any one of <2> to <5>, the method including:

placing the one end side of the chromatographic strip at the projected portion formed on the support surface of the chromatographic strip support tool in a manner that the extremity of the chromatographic strip at the one end side opposite to a side at which an analyte is supplied and the first abutting portion abut against each other and in a manner that at least the partial portion of the side surface of the chromatographic strip, the side surface being parallel with the longitudinal direction of the chromatographic strip, and the second abutting portion abut against each other; and in response to a detection at the predetermined location of the chromatographic strip, discerning the detection item of the display section, the detection item being displayed at a location corresponding to the predetermined location at which the detection occurs.

<11> The method of using the chromatographic strip support tool according to <9> or <10>, further including supplying the analyte to the chromatographic strip either before or after the placing of the one end side of the chromatographic strip at the projected portion formed on the support surface of the chromatographic strip support tool.

<12> The method of using the chromatographic strip support tool according to any one of <9> to <11>, further including pasting an adhesive label containing information regarding the analyte on the projected portion in a manner that the adhesive label extends across the chromatographic strip in a transverse direction of the chromatographic strip at the one end side, after the placing of the one end side of the chromatographic strip at the projected portion formed on the support surface of the chromatographic strip support tool.

<13> The method of using the chromatographic strip support tool according to any one of <9> to <12>, wherein the chromatographic strip is for either immunochromatography or nucleic acid chromatography.

<14> The method of using the chromatographic strip support tool according to any one of <9> to <13>, wherein the chromatographic strip is a lateral flow type.

Advantageous Effects of Invention

The present invention can solve the various problems in the related art, achieve the object described above, and provide a chromatographic strip support tool that minimizes occurrence of mistaken reading (mistaken detection) of a result indicating a successful detection (line coloring) due to misplacement of a chromatographic strip, and does not inhibit smooth development of an analyte, and a method of using the chromatographic strip support tool.

BRIEF DESCRIPTION OF DRAWINGS

FIG. 5A is an end surface view seen from a viewing location A in FIG. 3.

FIG. 5B is an end surface view seen from a viewing location B in FIG. 3.

FIG. 12 is a plan view illustrating an example of a chromatographic strip support tool according to a second embodiment of the present invention.

FIG. 13A is a cross-sectional view of FIG. 12 along an X-X' axis seen from a viewing location A in FIG. 12.

FIG. 13B is a cross-sectional view of FIG. 12 along a Y-Y' axis seen from a viewing location B in FIG. 12.

FIG. 14B is an end surface view seen from a viewing location B in FIG. 12.

FIG. 14C is an end surface view seen from a viewing location C in FIG. 12.

FIG. 18B is an end surface view seen from a viewing location B in FIG. 16.

DESCRIPTION OF EMBODIMENTS (Chromatographic Strip Support Tool)

The embodiments of the chromatographic strip support tool of the present invention will be described below with reference to the drawings. The present invention should not be construed as being limited to these embodiments.

First Embodiment

An example of the chromatographic strip support tool according to the first embodiment of the present invention will be described with reference to FIG. 1 to FIG. 5C. A chromatographic strip support tool 10 of the present invention does not encompass one that includes a chromatographic strip 15.

Figure 1:
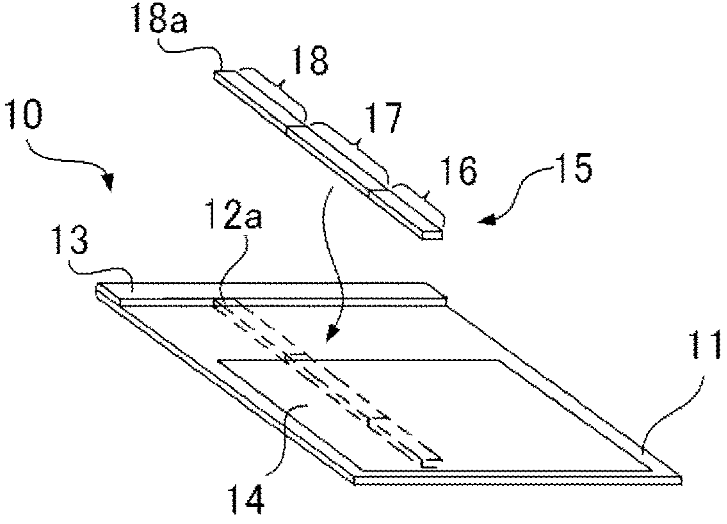
FIG. 1 is an oblique view illustrating an example of chromatographic strip support tool and an example of a chromatographic strip according to a first embodiment of the present invention.
Figure 2:
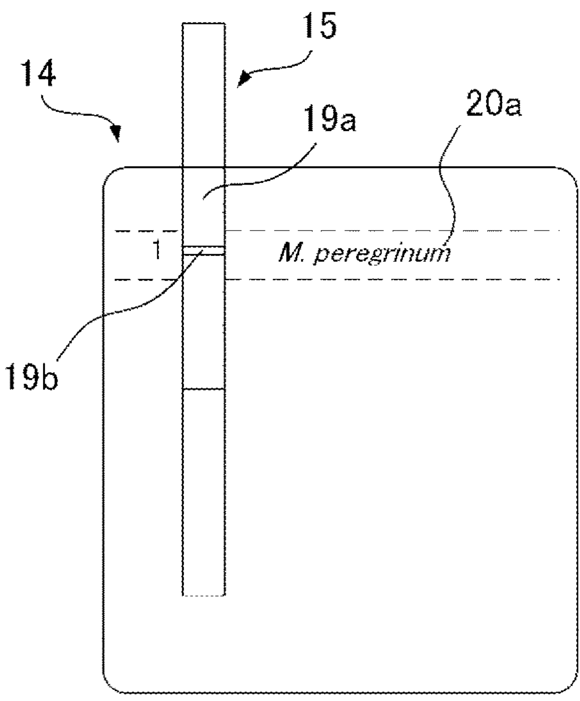
FIG. 2 is a schematic view illustrating an example of a display section when a chromatographic strip is placed on a support surface in a manner that an extremity of the chromatographic strip abuts against a first abutting portion.

In the example illustrated in FIG. 1 and FIG. 2, the chromatographic strip 15 includes an analyte supply section 16 to which an analyte is supplied, a membrane section 17 in which an analyte is developed, and an absorption pad section 18 configured to absorb the analyte. After an analyte is supplied to the analyte supply section 16 and developed with a developing solution, a line coloring 19*b* (color development on a test line), which occurs when a predetermined biological component is present, may become readable. In this way, the biological component contained in the supplied analyte can be detected.

The chromatographic strip exhibits a line coloring (color development on a test line) at a predetermined location when a predetermined biological component is present. The number of test lines is not particularly limited, may be appropriately selected in accordance with the intended purpose, and is preferably a plural number such as two or greater and ten or less.

A line coloring (color development on a test line) on the chromatographic strip may be exhibited by, for example, colloid particles formed of metals such as gold, silver, copper, and platinum, colored latexes obtained by coloring latexes with, for example, pigments and dyes, and silica nanoparticles obtained by immobilizing pigment molecules in silica particles. Among these, it is preferable to use colloid particles formed of gold (coloring in red), and colored latexes formed of water-dispersible high-molecular-weight polymers colored in, for example, blue and red.

Examples of the chromatographic strip include a chromatographic strip for immunochromatography and a chromatographic strip for nucleic acid chromatography. Examples of the types of the chromatographic strip include a lateral flow type and a dip stick type. Of these types, the lateral flow type is preferable.

In accordance with the intended purpose, the chromatographic strip can be used for various detection uses that are not particularly limited. For example, the chromatographic strip can be suitably used for detection uses in which accuracy in line coloring reading (accuracy in discerning) is particularly demanded, such as examination for infectious diseases, detection of allergens in foods, and food quality control (inspection for falsely labeled foods and genetically modified foods).

The biological molecule is not particularly limited and may be appropriately selected in accordance with the intended purpose. Examples of the biological molecule include a nucleic acid, a labeled nucleic acid, an amplified product of a nucleic acid, a protein, a microorganism, and a virus.

Figure 3:
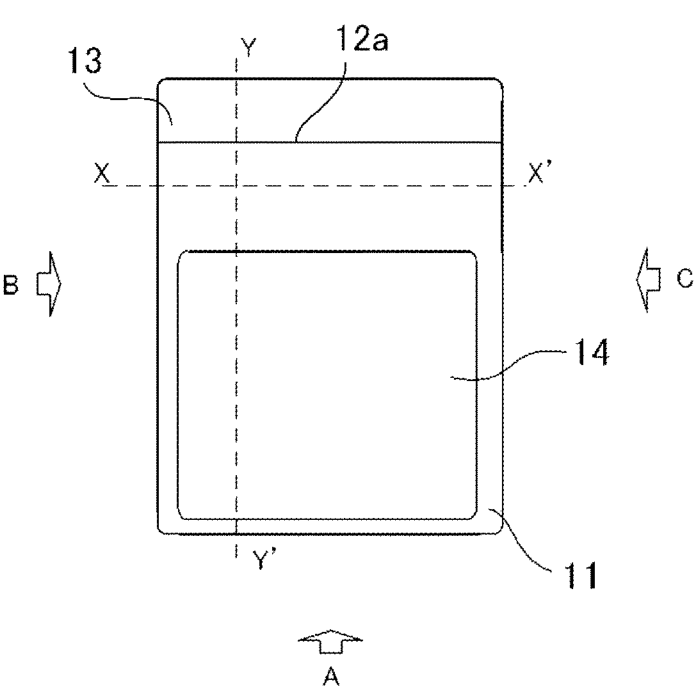
FIG. 3 is a plan view illustrating an example of a chromatographic strip support tool according to a first embodiment of the present invention.
Figure 4A:
FIG. 4A is a cross-sectional view of FIG. 3 along an X-X' axis seen from a viewing location A in FIG. 3.
Figure 4B:
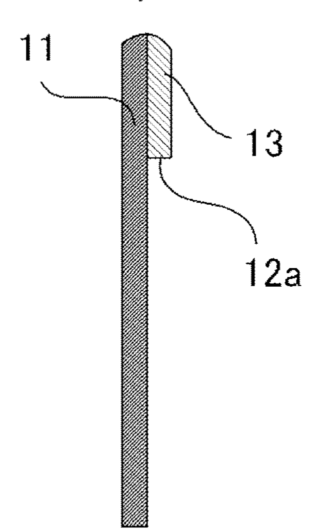
FIG. 4B is a cross-sectional view of FIG. 3 along a Y-Y' axis seen from a viewing location B in FIG. 3.
Figure 5C:
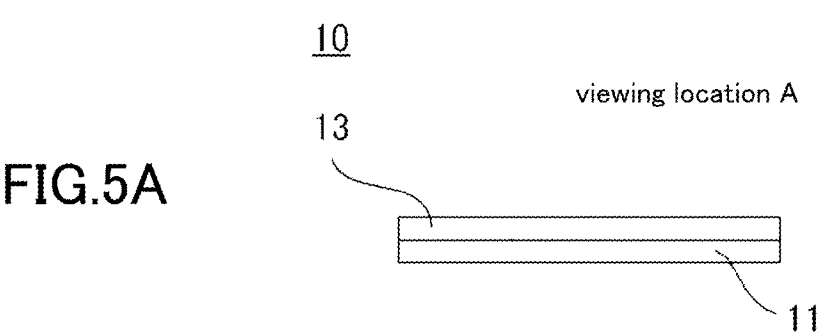
FIG. 5C is an end surface view seen from a viewing location C in FIG. 3.
Figure 5C:
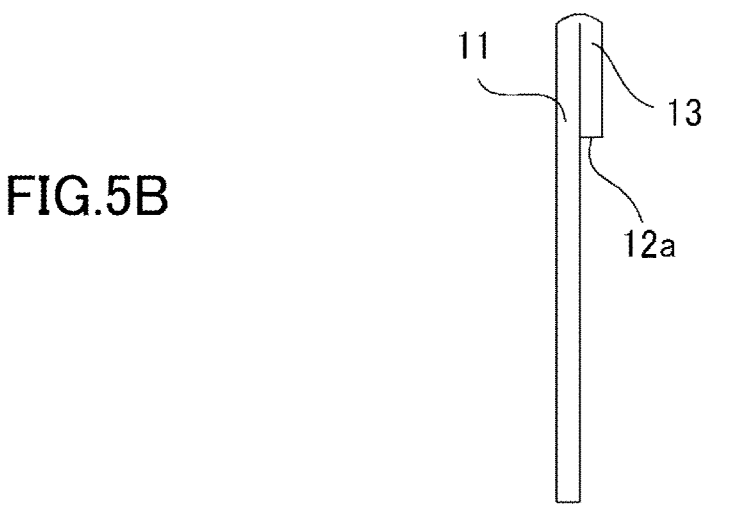

The chromatographic strip support tool 10 according to the first embodiment includes a support surface 11 that is continuous and on which the chromatographic strip 15 can be placed as illustrated in FIG. 1 and FIG. 3 to FIG. 5C, a projected portion 13 formed on the support surface 11 as illustrated in FIG. 1, FIG. 3, and FIG. 4B to FIG. 5C, and a display section 14 formed on the support surface 11 as illustrated in FIG. 1 to FIG. 3.

As the material of the support surface 11, the projected portion 13, and the display section 14, paper that is coated with a water shedding material and can be inhibited from being soaked with an analyte is used.

The projected portion 13 has a first abutting portion 12*a* that can abut against an extremity 18*a* of the chromatographic strip 15 placed (put) on the support surface 11, the extremity 18*a* being present at one end side (absorption pad section 18) of the chromatographic strip 15, as illustrated in FIG. 1, FIG. 3, FIG. 4B, FIG. 5B, and FIG. 5C.

FIG. 2 is a schematic view illustrating an example of the display section 14 when the chromatographic strip 15 is placed (put) on the support surface 11 in a manner that the extremity 18*a* of the chromatographic strip 15 abuts against the first abutting portion 12*a*.

The display section 14 has a detection item 20*a* as illustrated in FIG. 2. In FIG. 2, "M. peregrium" displayed as the detection item 20*a* represents a kind of a fungus belonging to acid-fast bacilli.

The detection item 20*a* is displayed at a location corresponding to a predetermined location 19*a* of the chromatographic strip 15, the predetermined location 19*a* being a location at which a result indicating a successful detection (line coloring 19*b*) may be obtained, i.e., the line coloring 19*b* may be observed.

Examples of the location corresponding to the predetermined location 19*a* includes a location adjacent to the predetermined location 19*a* on either the left-hand side or the right-hand side, and a location beyond a lead line leading out from the predetermined location 19*a*.

Figures 6A, 6B, 6C, 7A:
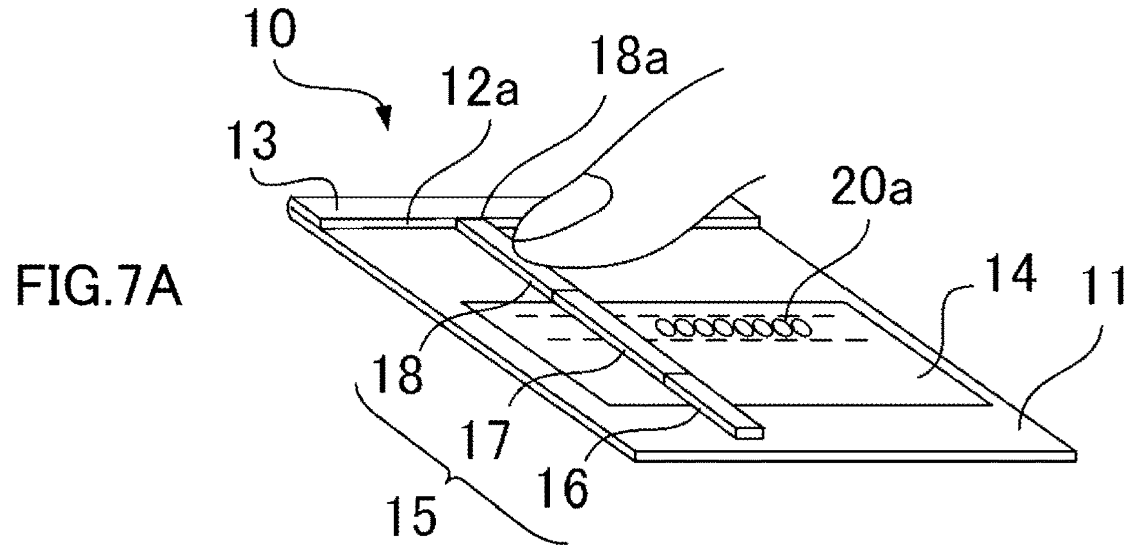
FIG. 6A is an oblique view illustrating an example of a chromatographic strip support tool according to a first embodiment of the present invention, including a support surface 11 and a foldable portion 22 continuous with the support surface 11 via a folding line 21.
FIG. 6B is an oblique view illustrating an example of a chromatographic strip support tool according to a first embodiment of the present invention in a state of a foldable portion 22 being folded along a folding line 21.
FIG. 6C is an oblique view illustrating an example of a chromatographic strip support tool according to a first embodiment, of the present invention in a state of a foldable portion 22 being fixed in a manner to abut against a support surface 11.
FIG. 7A is a schematic view illustrating an example of a method of using a chromatographic strip support tool according to a first, embodiment of the present invention.

The chromatographic strip support tool 10 includes a support surface 11 that is continuous and on which the chromatographic strip 15 can be placed, and a foldable portion 22 continuous with the support surface 11 via a folding line 21 as illustrated in FIG. 6A.

When the foldable portion 22 is folded along the folding line 21 as illustrated in FIG. 6B and is made to abut against the support surface 11 as illustrated in FIG. 6C, the foldable portion 22 becomes fixed in a manner to form the projected portion 13 having the first abutting portion 12*a* that can abut against the extremity 18*a* of the chromatographic strip 15 placed (put) on the support surface 11, the extremity 18*a* being present at the one end side (absorption pad section 18) of the chromatographic strip 15.

The foldable portion 22 is fixed by bonding with an adhesive agent.

Handlings and workings of the chromatographic strip support tool configured as described above will be described below with reference to FIG. 1 and FIG. 2.

When placing (putting) the chromatographic strip 15 on the support surface 11 of the chromatographic strip support tool 10, the chromatographic strip 15 is placed (put) on the support surface in a manner that the extremity 18*a* of the chromatographic strip 15, present at the one end side (absorption pad section 18) opposite to the side at which the analyte supply section 16 is present, and the first abutting portion 12*a* abut against each other as illustrated in FIG. 1. This makes the location at which the detection item 20*a* of the display section 14 of the chromatographic strip support tool 10 is displayed positionally correspond to a result indicating a successful detection (line coloring 19*b*) that may be obtained at the predetermined location 19*a* of the chromatographic strip 15 as illustrated in FIG. 2. As a result, it is possible to minimize occurrence of mistaken reading (mistaken detection) of the result indicating a successful detection (line coloring 19*b*) due to misplacement of the chromatographic strip 15.

The projected portion 13 abuts only against the absorption pad section 18 of the chromatographic strip 15 and does not abut against the membrane section 17. This makes it possible to obtain the correct result indicating a successful detection without inhibiting smooth development (flow) of the analyte. The absorption pad section 18, which is provided in order to minimize backflow of the analyte, does not inhibit development (flow) of the analyte even though the absorption pad section 18 abuts against the projected portion 13.

Examples

The modes for carrying out the chromatographic strip support tool according to the first embodiment will be described with reference to FIG. 7A to FIG. 7D.

As illustrated in FIG. 7A, the chromatographic strip 15 is placed (put) on the support surface 11 of the chromatographic strip support tool 10 in a manner that the extremity 18*a* of the absorption pad section 18 of the chromatographic strip 15 and the first abutting portion 12*a* abut against each other.

Figure 7B:
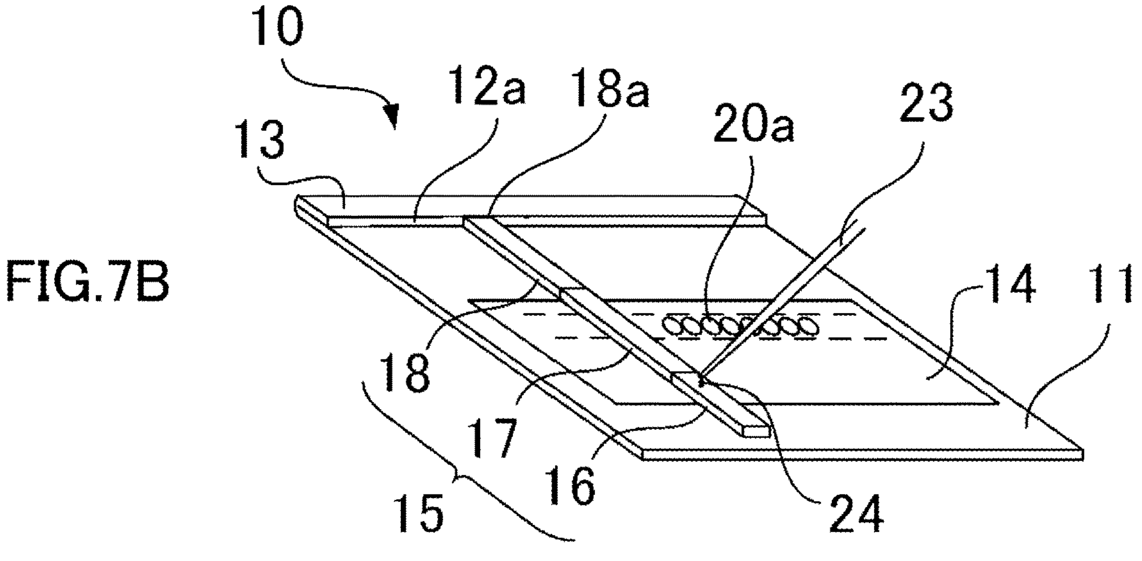
FIG. 7B is a schematic view illustrating an example of a method of using a chromatographic strip support tool according to a first embodiment of the present invention.

As illustrated in FIG. 7B, using a sample adding tool 23, a liquid analyte 24 is added onto the analyte supply section 16 of the chromatographic strip 15.

Figure 7C:
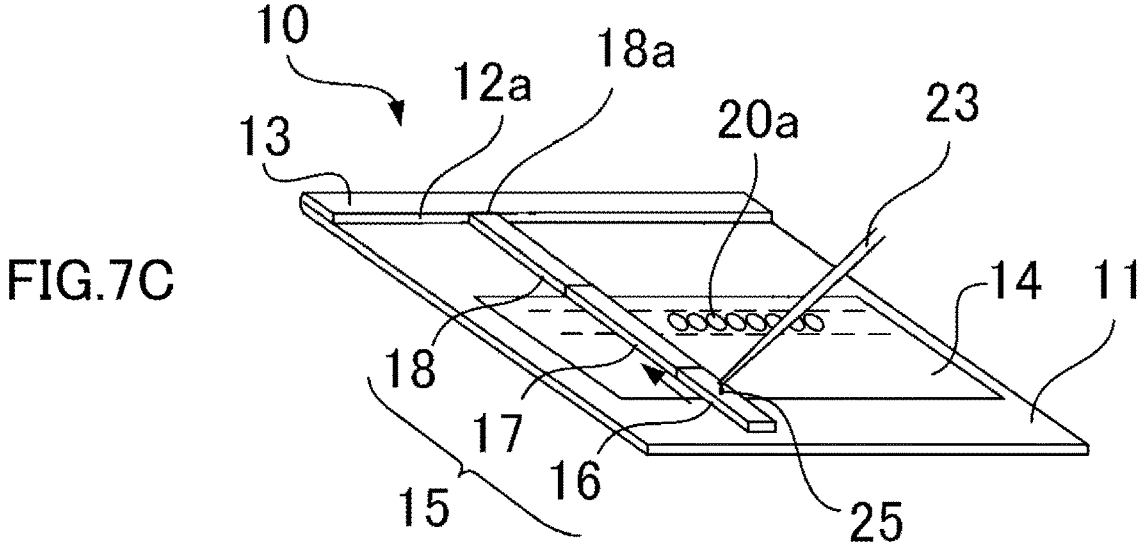
FIG. 7C is a schematic view illustrating an example of a method of using a chromatographic strip support tool according to a first embodiment of the present invention.

As illustrated in FIG. 7C, using the sample adding tool 23, a developing solution 25 is added onto a location on the analyte supply section 16 of the chromatographic strip 15, the location being closer to the extremity of the analyte supply section 16 than is the location onto which the analyte 24 is added. By the developing solution 25 being added, the analyte 24 and the developing solution 25 are developed through the membrane section 17 in the direction indicated by an arrow in FIG. 7C. Here, the side surfaces of the membrane section 17 do not abut against anything at all. Hence, smooth development of the analyte 24 is not inhibited.

Figure 7D:
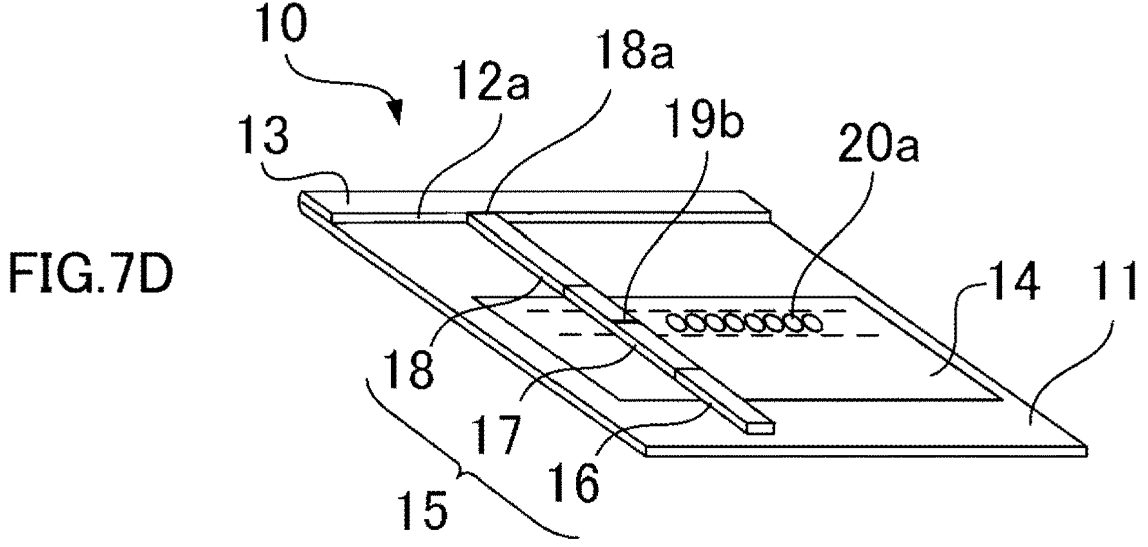
FIG. 7D is a schematic view illustrating an example of a method of using a chromatographic strip support tool according to a first embodiment of the present invention.

As illustrated in FIG. 7D, when a predetermined biological molecule is contained in the analyte 24, the line coloring 19*b* is detected, i.e., the line coloring 19*b* is observed at the predetermined location of the membrane section 17 a few minutes after the developing solution 25 is developed. Hence, the detection item 20*a* of the display section 14 displayed at the location corresponding to the predetermined location is discerned.

Since the location of the line coloring 19*b* corresponds to the location of the detection item 20*a* displayed on the display section 14 of the chromatographic strip support tool 10, it is possible to discern that the analyte 24 contains the predetermined biological molecule.

Modifications of the First Embodiment

In the first embodiment, the display section 14 illustrated in FIG. 2 is formed on the support surface 11. In a modification of the first embodiment, a display section 14 illustrated in FIG. 8 may be formed on the support surface 11.

Figure 8:
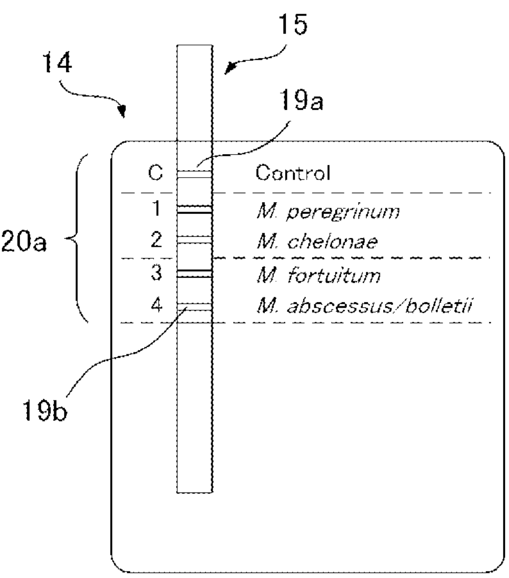
FIG. 8 is a schematic view illustrating an example of a display section 14 according to a modification of a first embodiment of the present invention.

The display section 14 illustrated in FIG. 8 displays a plurality of detection items 20*a* corresponding to a plurality of predetermined locations 19*a* of the chromatographic strip respectively. Hence, it is possible to obtain a plurality of discerning results (diagnosing results) by one testing. In FIG. 8, "M. peregrium", "*M. chelonae", "M. fortuitum*" and "*M. abscessus*/bolletii" displayed as the detection items 20*a* represent different kinds of fungi belonging to acid-fast bacilli respectively.

A detection item transcribing section 20*b* is not particularly limited and may be appropriately selected in accordance with the intended purpose. Examples of the detection item transcribing section 20*b* include a scantron and a checkbox.

The method for recording in the detection item transcribing section 20*b* is not particularly limited and may be appropriately selected in accordance with the intended purpose. Examples of the method include addition of a checkmark by a writing material, solid fill-out, fill-in with a symbol, and pasting of a label.

Recording in the detection item transcribing section 20*b* is performed when the line coloring 19*b* occurs at the predetermined location 19*a*. Hence, even if the line coloring 19*b* on the predetermined location 19*a* discolors over time, the discerning result (diagnosing result) can be seen. Moreover, when color development on the line coloring 19*b* is weak and cannot be read by a device even though it can be visually perceived by a bare eye, it is possible to read the line coloring correctly based on the transcribed information, and to derive the discerning result (diagnosing result) on the chromatographic strip correctly.

The location of the detection item transcribing section 20*b* is not particularly limited, may be appropriately selected in accordance with the intended purpose, and is preferably a location corresponding to the detection item 20*a*.

Examples of the location corresponding to the detection item 20*a* includes a location adjacent to the detection item 20*a* on either the left-hand side or the right-hand side, and a location beyond a lead line leading out from the predetermined location.

Figure 9:
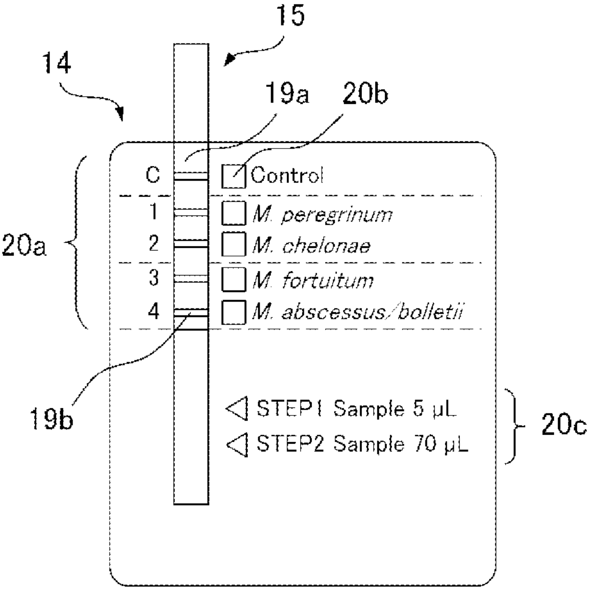
FIG. 9 is a schematic view illustrating an example of a display section 14 according to a modification of a first embodiment of the present invention.

An auxiliary item 20*c* is not particularly limited and may be appropriately selected in accordance with the intended purpose. Examples of the auxiliary item 20*c* include an indication of the location at which to add an analyte, an indication of the order to add an analyte, an indication of the amount by which to add an analyte, and an indication of a name. In FIG. 9, "ΔSTEP1 Sample 5 μL" displayed as the auxiliary item 20*c* represents that "the first thing to do is to add a sample (analyte) by 5 μL to the location indicated by the Δ symbol (the location being the analyte supply section 16 of the chromatographic strip 15)", and "ΔSTEP2 Sample 70 μL," displayed as the auxiliary item 20*c* represents that "the second thing to do is to add a sample (developing solution) by 70 μL to the location indicated by the Δ symbol (the location being the analyte supply section 16 of the chromatographic strip 15)". In this way, the auxiliary item 20*c* enables even an inexperienced person to use the chromatographic strip support tool.

In the first embodiment, paper coated with a water shedding material is used as the material of the support surface 11, the projected portion 13, and the display section 14. In a modification 3 of the first embodiment, for example, plastics and metals having a water shedding property may be used as the material. By using, for example, plastics and metals having a water shedding property, it is possible to better inhibit soaking with an analyte.

Examples of the plastics include polyethylene, polystyrene, polypropylene, vinyl chloride, and silicone.

Examples of the metals include aluminum and stainless steel.

Figure 10:
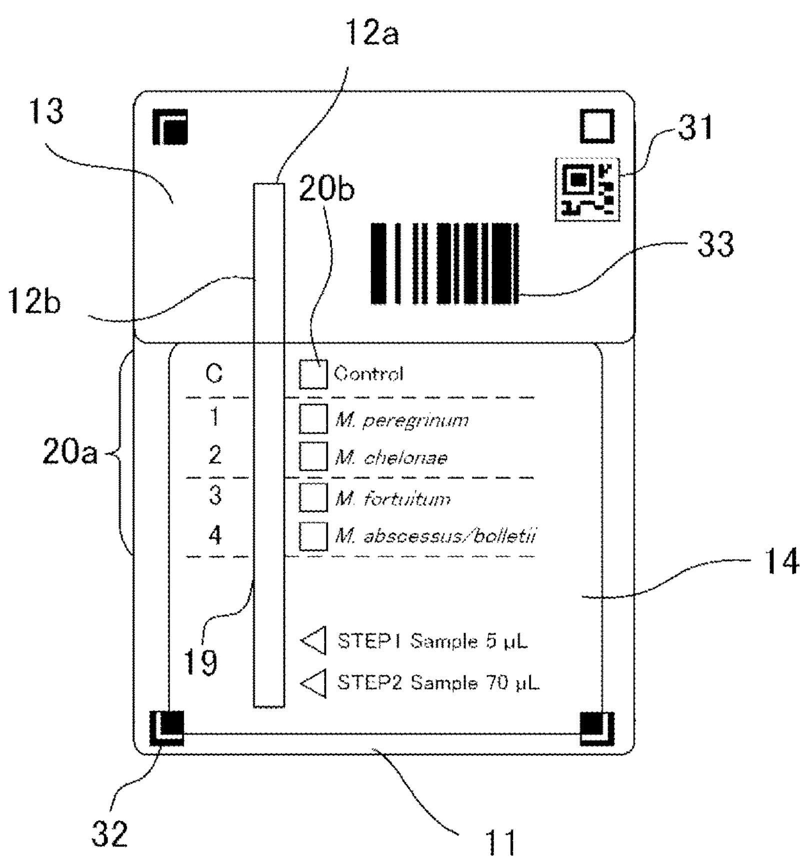
FIG. 10 is a plan view illustrating an example of the styles in which various kinds of information held on a chromatographic strip support tool are displayed in a modification of a first embodiment of the present invention.

A modification of the first embodiment may include a product identification information indication 31, an information acquisition assisting marker section 32, and an analyte information indication 33 as illustrated in FIG. 10.

The product identification information indication 31 is not particularly limited and may be appropriately selected in accordance with the intended purpose. Examples of the product identification information indication 31 include an adhesive label for a two-dimensional code (QR code (registered trademark)) as illustrated in FIG. 10. It is preferable to record the product identification information (e.g., an ID) of the chromatographic strip support tool 10 in the product identification information indication 31. For example, the product identification information may be selectable from a terminal device owned by a user.

The product identification information is not particularly limited and may be appropriately selected in accordance with the intended purpose so long as the product identification information is information regarding the analyte. Examples of the product identification information include the name of the chromatographic strip support tool (product), a detection item, a product number, a product lot number, and a use-by date.

The location at which the product identification information indication 31 (adhesive label 31) is pasted is not particularly limited and may be appropriately selected in accordance with the intended purpose. Examples of the location include the support surface 11, the projected portion 13, and the display section 14. Among these options, the projected portion 13 is preferable, and such a region of the projected portion 13 as extending across the chromatographic strip 15 in a transverse direction of the chromatographic strip 15 at the one end side is more preferable. This makes it possible to inhibit detachment of the chromatographic strip 15 from the chromatographic strip support tool 10.

The information acquisition assisting marker section 32 is not particularly limited and may be appropriately selected in accordance with the intended purpose so long as the information acquisition assisting marker section 32 can be used as a marker by which to align the chromatographic strip support tool 10 in the right location and orientation when capturing an image of the chromatographic strip support tool 10 on the whole using an information acquiring unit such as an image capturing unit and acquiring information. It is preferable to provide the information acquisition assisting marker section 32 at the four corners of the chromatographic strip support tool 10 when the planar shape of the chromatographic strip support tool 10 is a quadrangular shape as illustrated in FIG. 10.

The analyte information indication 33 is not particularly limited and may be appropriately selected in accordance with the intended purpose. Examples of the analyte information indication 33 include a barcode as illustrated in FIG. 10. The analyte information is not particularly limited and may be appropriately selected in accordance with the intended purpose so long as the analyte information is information regarding the analyte supplied to the chromatographic strip. Examples of the analyte information include information indicating the subject who has donated the analyte, information indicating the date on which the analyte is collected, and information indicating, for example, the hospital at which the analyte is collected.

In the first embodiment, the foldable portion 22 is folded along the folding line 21, made to abut against the support surface 11, and fixed. In a modification of the first embodiment, the projected portion 13 may be laminated and fixed on the support surface 11.

The fixing method is not particularly limited and may be appropriately selected in accordance with the intended purpose so long as two or more plate materials can be joined. Examples of the fixing method include fixing by an adhesive agent.

In the first embodiment, the line coloring 19*b* at the predetermined location 19*a* of the chromatographic strip 15 is detected by visual observation. In a modification of the first embodiment, light that cannot be detected by visual observation under visible light but becomes an observable emission under irradiation with exciting light such as an ultraviolet ray or an infrared ray, or light or coloring that occurs when an external stimulus such as heat, pressure, electricity, and sound is applied may be detected by visual observation. Coloring may occur not only in a line shape, but in a dot shape, a letter shape, and a symbol shape.

In the first embodiment, the analyte is supplied to the analyte supply section 16 after the one end side (absorption pad section 18) of the chromatographic strip 15 is placed (put) at the projected portion 13 formed on the support surface 11 of the chromatographic strip support tool 10. In a modification of the first embodiment, the analyte may be supplied to the analyte supply section 16 before the one end side of the chromatographic strip 15 is placed (put) at the projected portion 13 formed on the support surface 11 of the chromatographic strip support tool 10.

Second Embodiment

An example of the chromatographic strip support tool according to the second embodiment of the present invention will be described with reference to FIG. 11 to FIG. 14C.

Any components that are the same as those included in the modes already described in the first embodiment will be denoted by the same reference numerals, and descriptions of such components will be skipped.

Figure 11:
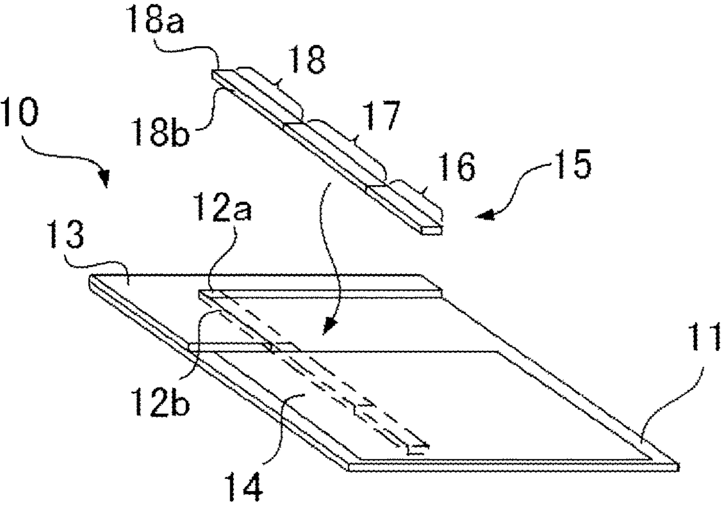
FIG. 11 is an oblique view illustrating an example of a chromatographic strip support tool and an example of a chromatographic strip according to a second embodiment of the present invention.
Figure 14A:
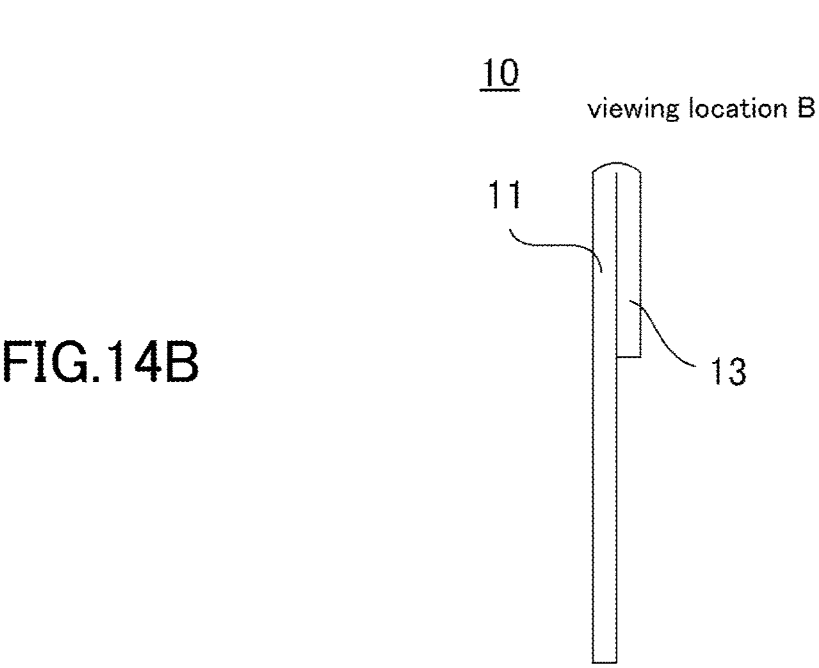
FIG. 14A is an end surface view seen from a viewing location A in FIG. 12.
Figure 14A:
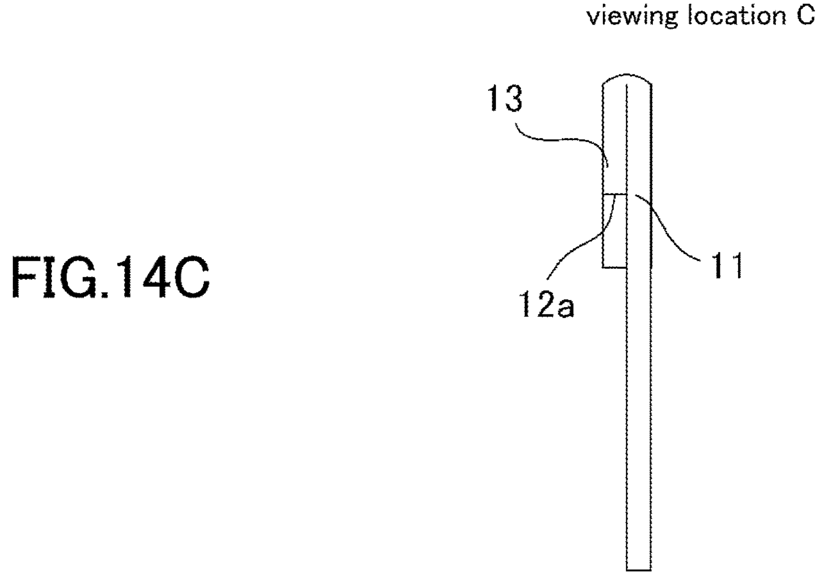

The chromatographic strip support tool 10 according to the second embodiment includes a support surface 11 that is continuous and on which a chromatographic strip 15 can be placed and a projected portion 13 formed on the support surface 11 as illustrated in FIG. 11 to FIG. 14C, and a display section 14 formed on the support surface 11 as illustrated in FIG. 11 and FIG. 12.

The projected portion 13 in the second embodiment has a first abutting portion 12*a* that can abut against an extremity 18*a* of the chromatographic strip 15 placed (put) on the support surface 11, the extremity 18*a* being present at one end side (absorption pad section 18) of the chromatographic strip 15, and a second abutting portion 12*b* that can abut against at least a partial portion of a side surface 18*b* of the chromatographic strip 15, the partial portion being present at the one end side (absorption pad section 18) of the chromatographic strip 15, the side surface 18*b* being parallel with the longitudinal direction of the chromatographic strip 15 as illustrated in FIG. 11 to FIG. 13A and FIG. 14C.

When placing (putting) the chromatographic strip 15 on the support surface 11, the chromatographic strip 15 is placed (put) on the support surface in a manner that the extremity 18*a* of the chromatographic strip 15 at the one end side (absorption pad section 18) opposite to the side at which the analyte supply section 16 is present and the first abutting portion 12*a* abut against each other and at least the partial portion of the side surface 18*b* of the chromatographic strip 15, the side surface 18*b* being parallel with the longitudinal direction of the chromatographic strip 15, and the second abutting portion 12*b* abut against each other. This makes it possible to inhibit mistaken reading of a result indicating a successful detection due to misplacement of the chromatographic strip 15.

As regards the chromatographic strip support tool 10 according to the second embodiment, it is preferable that the first abutting portion 12*a* and the second abutting portion 12*b* of the projected portion 13 be disposed at locations at which the first abutting portion 12*a* and the second abutting portion 12*b* are orthogonal to each other in a plan view of the support surface 11 as illustrated in FIG. 12. It is also preferable that one end of the first abutting portion 12*a* and one end of the second abutting portion 12*b* contact each other in the plan view of the support surface 11.

Modifications of the Second Embodiment

For example, modifications of the second embodiment may be the same as the modifications of the first embodiment.

Third Embodiment

An example of the chromatographic strip support tool according to the third embodiment of the present invention will be described with reference to FIG. 15 to FIG. 19G.

Any components that are the same as those included in the modes already described in the first embodiment will be denoted by the same reference numerals, and descriptions of such components will be skipped.

Figures 15, 16, 17A:
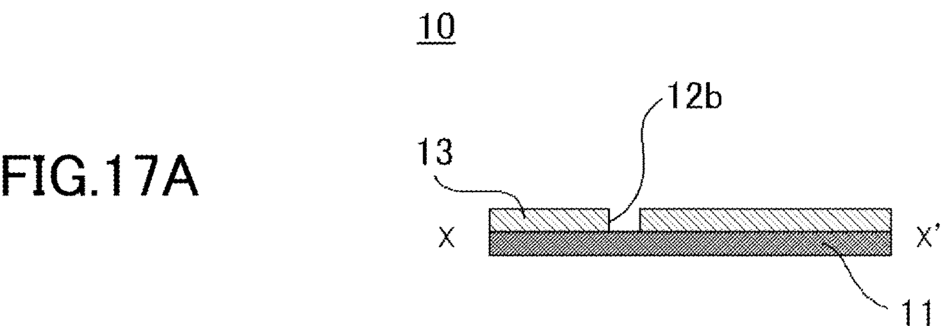
FIG. 15 is an oblique view illustrating an example of a chromatographic strip support tool and an example of a chromatographic strip according to a third embodiment of the present invention.
FIG. 16 is a plan view illustrating an example of a chromatographic strip support tool according to a third embodiment of the present invention.
FIG. 17A is a cross-sectional view of FIG. 16 along an X-X' axis seen from a viewing location A in FIG. 16.
Figure 17B:
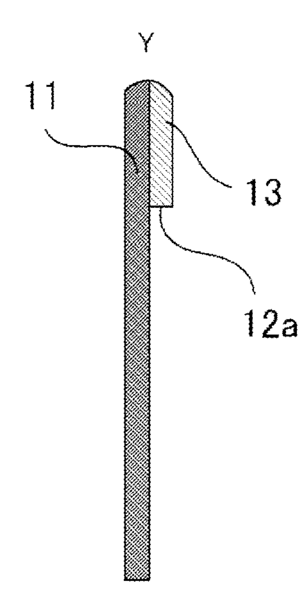
FIG. 17B is a cross-sectional view of FIG. 16 along a Y-Y' axis seen from a viewing location B in FIG. 16.
Figure 17B:
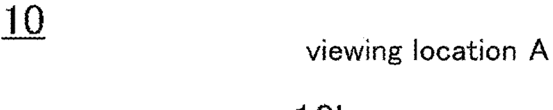
Figure 18A:
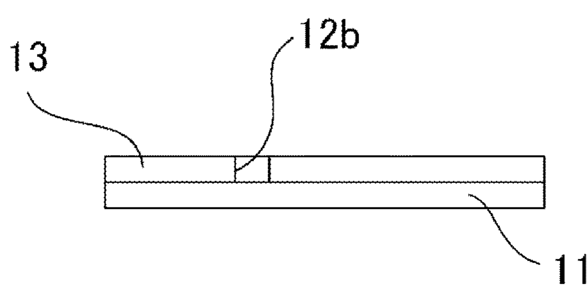
FIG. 18A is an end surface view seen from a viewing location A in FIG. 16.
Figure 18A:
Figure 18A:
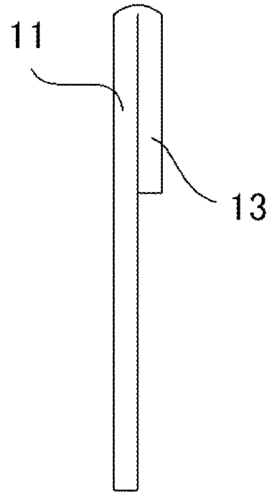
Figure 18C:
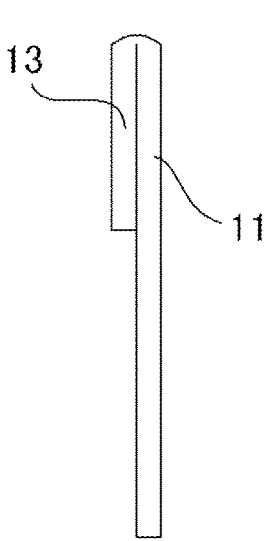
FIG. 18C is an end surface view seen from a viewing location C in FIG. 16.
Figure 19A:
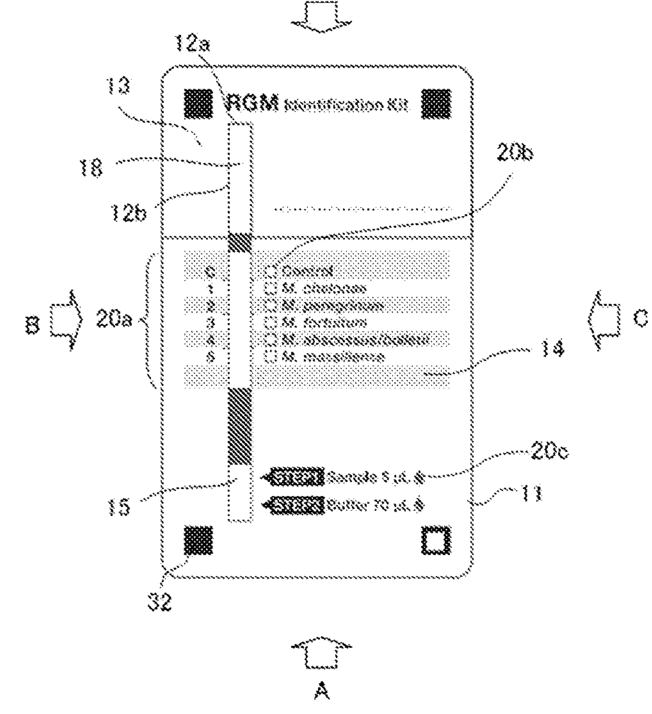
FIG. 19A is a plan view illustrating another example of a chromatographic strip support tool according to a third embodiment of the present invention (front surface).
Figure 19B:
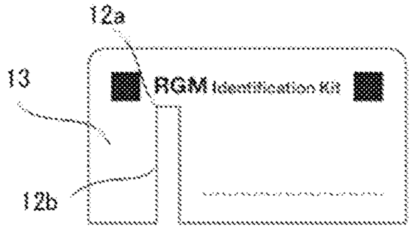
FIG. 19B is a plan view illustrating an example of a projected portion 13 of FIG. 19A.
Figure 19C:
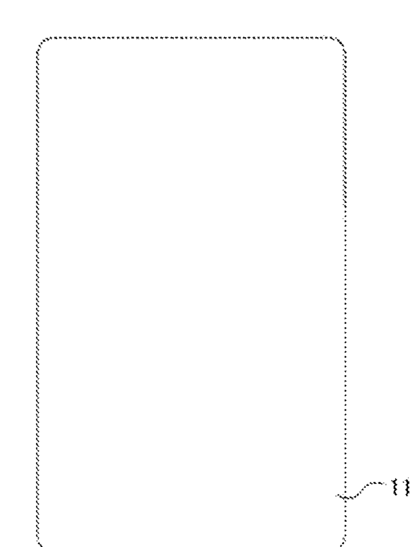
FIG. 19C is a plan view illustrating another example of a chromatographic strip support tool according to a first embodiment of the present invention (back surface).
Figure 19D:
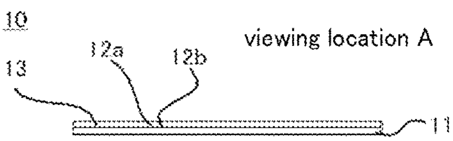
FIG. 19D is an end surface view seen from a viewing location A in FIG. 19A.
Figure 19E:
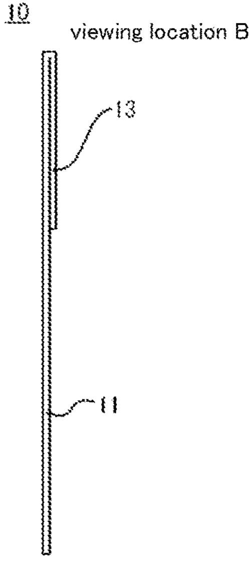
FIG. 19E is an end surface view seen from a viewing location B in FIG. 19A.
Figure 19F:
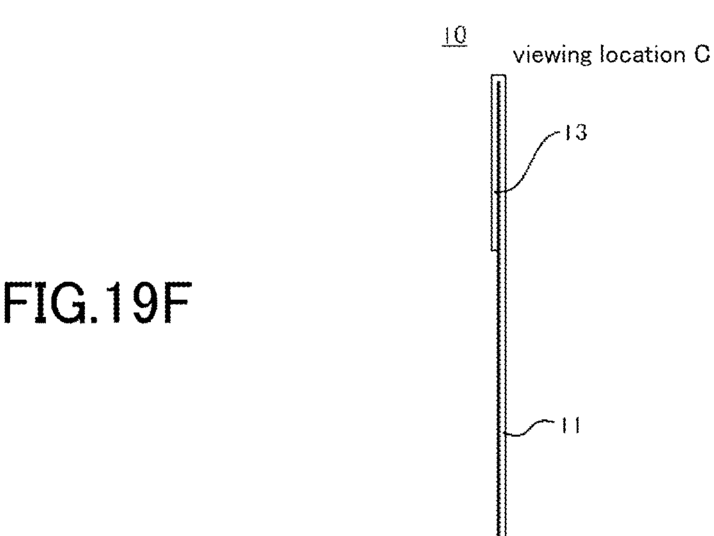
FIG. 19F is an end surface view seen from a viewing location C in FIG. 19A.
Figure 19G:
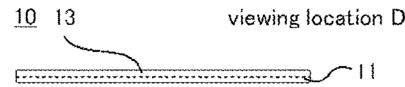
FIG. 19G is an end surface view seen from a viewing location D in FIG. 19A.
Figure 20A:
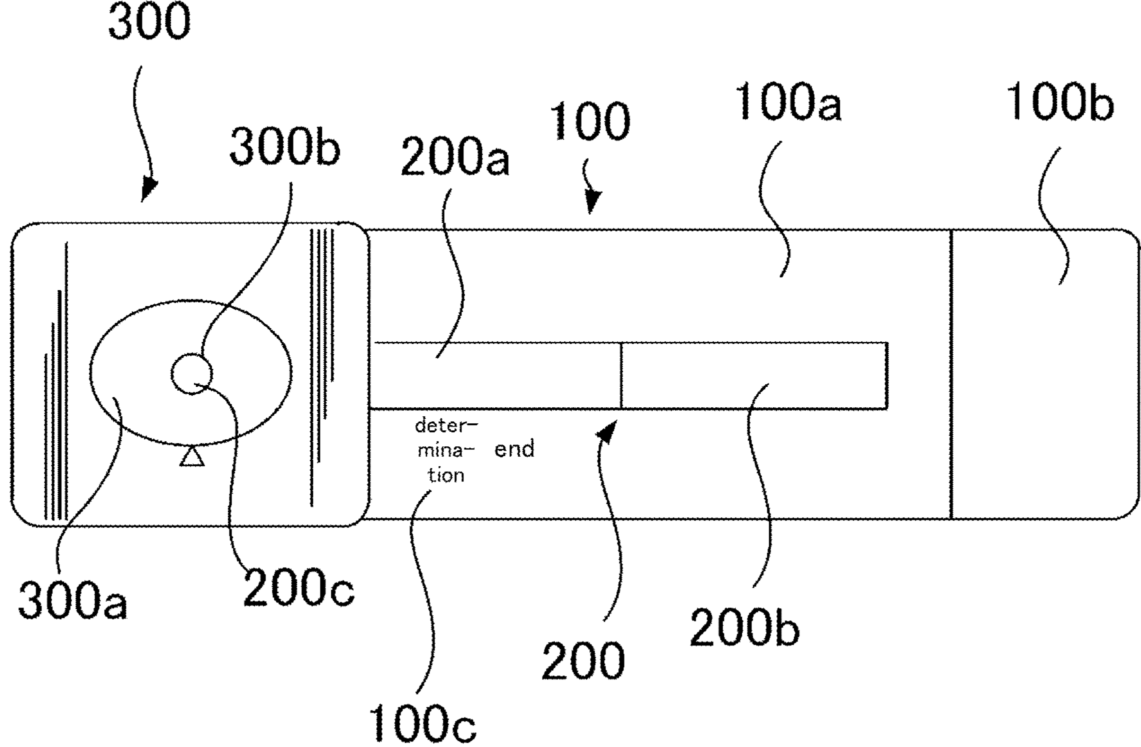
FIG. 20A is a plan view illustrating an example of a testing device including an existing chromatographic strip.
Figure 20B:
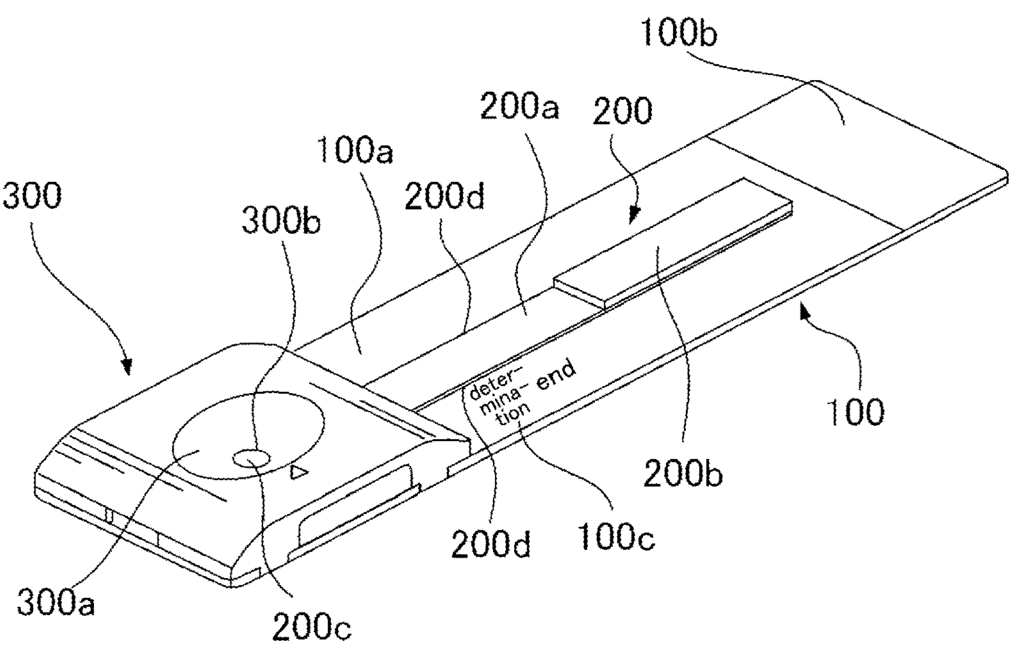
FIG. 20B is an oblique view illustrating an example of a testing device including an existing chromatographic strip.
Figure 20C:
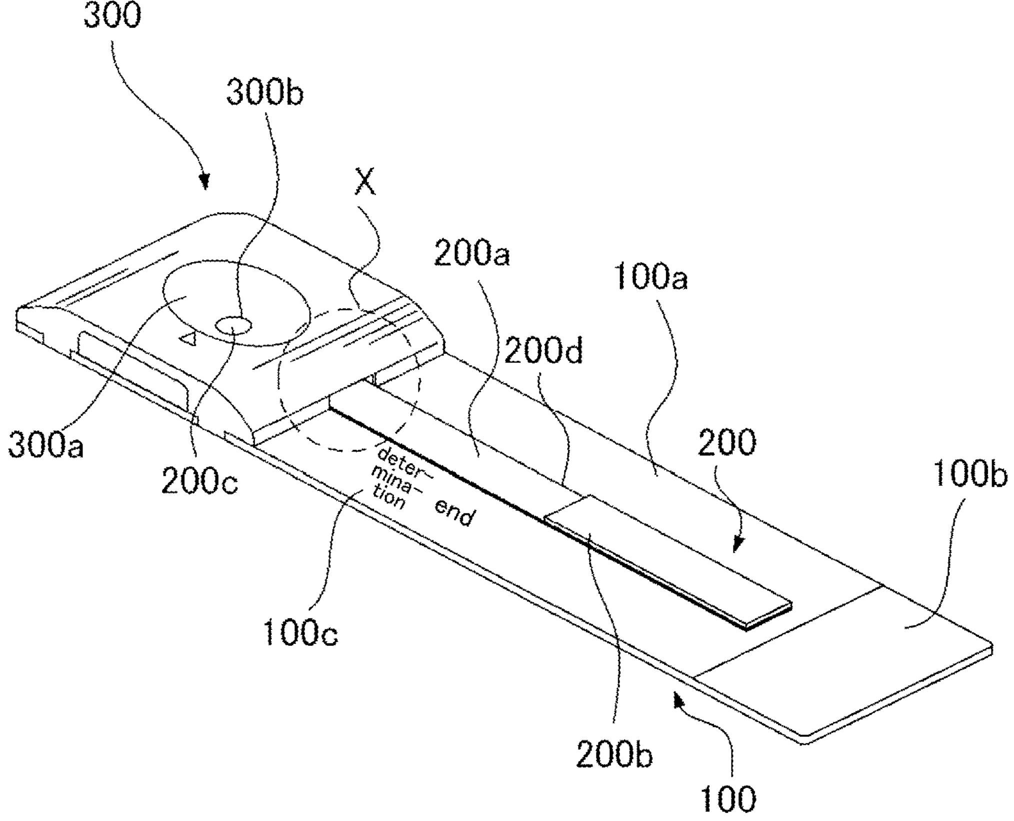
FIG. 20C is an oblique view illustrating an example of a testing device including an existing chromatographic strip.
Figure 20D:
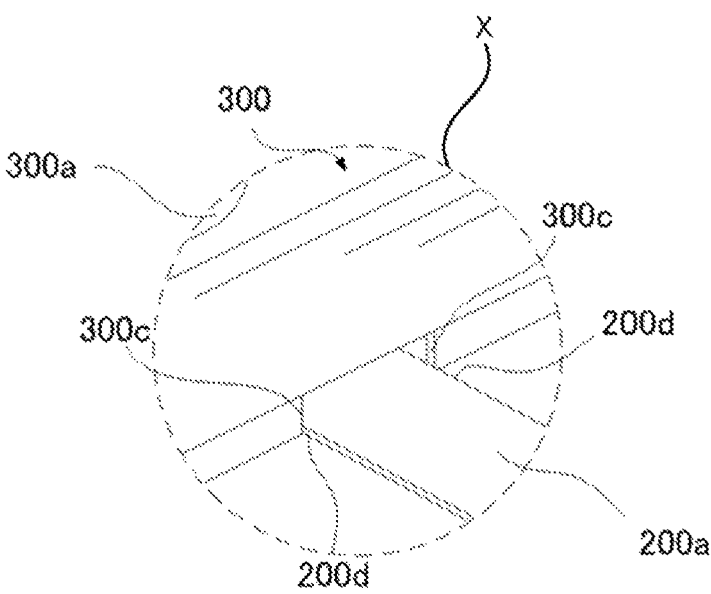
FIG. 20D is an expanded view of a portion X enclosed by a broken line in FIG. 20C.

The chromatographic strip support tool 10 according to the third embodiment includes a support surface 11 that is continuous and on which a chromatographic strip 15 can be placed and a projected portion 13 formed on the support surface 11 as illustrated in FIG. 15 to FIG. 19G, and a display section 14 formed on the support surface 11 as illustrated in FIG. 15, FIG. 16, and FIG. 19A.

The projected portion 13 in the third embodiment has a first abutting portion 12*a* that can abut against an extremity 18*a* of the chromatographic strip 15 placed (put) on the support surface 11, the extremity 18*a* being present at one end side (absorption pad section 18) of the chromatographic strip 15, and a pair of second abutting portions 12*b* that can abut against at least partial portions of a pair of side surfaces 18*b* of the chromatographic strip 15 respectively, the partial portions being present at the one end side (absorption pad section 18) of the chromatographic strip 15, the pair of side surfaces 18*b* being parallel with the longitudinal direction of the chromatographic strip 15 as illustrated in FIG. 15 and FIG. 19A.

When placing (putting) the chromatographic strip 15 on the support surface 11, the chromatographic strip 15 is placed (put) on the support surface in a manner that the extremity 18*a* of the chromatographic strip 15 at the one end side (absorption pad section 18) opposite to the side at which the analyte supply section 16 is present and the first abutting portion 12*a* abut against each other and at least the partial portions of the pair of side surfaces 18*b* of the chromatographic strip 15, the pair of side surfaces 18*b* being parallel with the longitudinal direction of the chromatographic strip 15, and the pair of second abutting portions 12*b* abut against each other respectively. This makes it possible to better inhibit mistaken reading of a result indicating a successful detection due to misplacement of the chromatographic strip 15.

Modifications of the Third Embodiment

For example, modifications of the third embodiment may be the same as the modifications of the first embodiment.

REFERENCE SIGNS LIST

10: chromatographic strip support tool
11: support surface
12*a*: first abutting portion
12*b*: second abutting portion
13: projected portion
14: display section
15: chromatographic strip
16: analyte supply section
17: membrane section
18: absorption pad section
18*a*: extremity
18*b*: side surface
19*a*: predetermined location
19*b*: line coloring
20*a*: detection item
20*b*: detection item transcribing section (region of a scantron)
20*c*: auxiliary item
21: folding line
22: foldable portion
23: sample adding tool
24: analyte
25: developing solution
31: product identification information indication
32: information acquisition assisting marker section
33: analyte information indication
100: card-shaped support
100*a*: printed surface
100*b*: analyte name display field
100*c*: detection item
200*a*: determination region
200*b*: liquid absorbing section
200*c*: sample dropping section
200*d*: side surface
300: partial cover
300*a*: dent portion
300*b*: dropping hole
300*c*: opening portion

The invention claimed is:

1. A chromatographic strip support tool comprising:

a support surface that is continuous and on which a chromatographic strip can be placed, the chromatographic strip including an analyte supply section to which an analyte is supplied, a membrane section in which the analyte is developed, and an absorption pad section configured to absorb the analyte, the analyte supply section, the membrane section, and the absorption pad section being provided in this order;

a projected portion formed on the support surface and having a first abutting portion that can abut against an extremity of the chromatographic strip placed on the support surface, the extremity being present at one end side of the chromatographic strip; and a display section formed on the support surface and including a detection item displayed in a manner to correspond to a predetermined location of the chromatographic strip when the chromatographic strip is placed on the support surface in a manner that the extremity of the chromatographic strip abuts against the first abutting portion, wherein the projected portion abuts only against the absorption pad section of the chromatographic strip, the chromatographic strip support tool does not have a projected portion that abuts against a section of the chromatographic strip other than the absorption pad section, and the support surface is completely exposed.

2. The chromatographic strip support tool according to claim 1, wherein the projected portion has a second abutting portion that can abut against at least a partial portion of a side surface of the chromatographic strip placed on the support surface, the partial portion of the side surface being present at the one end side of the chromatographic strip, the side surface being parallel with a longitudinal direction of the chromatographic strip, and the display section includes the detection item displayed in a manner to correspond to the predetermined location of the chromatographic strip when the chromatographic strip is placed on the support surface in a manner that the extremity of the chromatographic strip abuts against the first abutting portion and the side surface of the chromatographic strip abuts against the second abutting portion.

3. The chromatographic strip support tool according to claim 2, wherein when the support surface is seen in a plan view perspective, the first abutting portion and the second abutting portion of the projected portion are at locations at which the first abutting portion and the second abutting portion are orthogonal to each other.

4. The chromatographic strip support tool according to claim 3, wherein when the support surface is seen in the plan view perspective, the first abutting portion and the second abutting portion of the projected portion are at the locations at which the first abutting portion and the second abutting portion are orthogonal to each other and one end of the first abutting portion and one end of the second abutting portion contact each other.

5. The chromatographic strip support tool according to claim 2, wherein the second abutting portion includes paired portions that can abut against at least partial portions of a pair of side surfaces of the chromatographic strip respectively, the pair of side surfaces being parallel with the longitudinal direction of the chromatographic strip.

6. The chromatographic strip support tool according to claim 1, wherein the display section includes a plurality of detection items displayed in a manner to correspond to a plurality of predetermined locations of the chromatographic strip respectively.

7. The chromatographic strip support tool according to claim 1, wherein the chromatographic strip support tool is configured such that the side surfaces of the membrane section do not abut against the chromatographic strip support tool.

8. A method of using the chromatographic strip support tool according to claim 1, the method comprising:

placing the one end side of the chromatographic strip at the projected portion formed on the support surface of the chromatographic strip support tool in a manner that the extremity of the chromatographic strip at the one end side opposite to a side at which an analyte is supplied and the first abutting portion abut against each other; and in response to a detection at the predetermined location of the chromatographic strip, discerning the detection item of the display section, the detection item being displayed at a location corresponding to the predetermined location at which the detection occurs.

9. A method of using the chromatographic strip support tool according to claim 2, the method comprising:

placing the one end side of the chromatographic strip at the projected portion formed on the support surface of the chromatographic strip support tool in a manner that the extremity of the chromatographic strip at the one end side opposite to a side at which an analyte is supplied and the first abutting portion abut against each other and in a manner that at least the partial portion of the side surface of the chromatographic strip, the side surface being parallel with the longitudinal direction of the chromatographic strip, and the second abutting portion abut against each other; and in response to a detection at the predetermined location of the chromatographic strip, discerning the detection item of the display section, the detection item being displayed at a location corresponding to the predetermined location at which the detection occurs.

10. The method of using the chromatographic strip support tool according to claim 8, further comprising supplying the analyte to the chromatographic strip either before or after the placing of the one end side of the chromatographic strip at the projected portion formed on the support surface of the chromatographic strip support tool.

11. The method of using the chromatographic strip support tool according to claim 8, further comprising pasting an adhesive label containing information regarding the analyte on the projected portion in a manner that the adhesive label extends across the chromatographic strip in a transverse direction of the chromatographic strip at the one end side, after the placing of the one end side of the chromatographic strip at the projected portion formed on the support surface of the chromatographic strip support tool.

12. The method of using the chromatographic strip support tool according to claim 8, wherein the chromatographic strip is for either immunochromatography or nucleic acid chromatography.

13. The method of using the chromatographic strip support tool according to claim 8, wherein the chromatographic strip is a lateral flow type.

* * * * *